United States Patent [19]

Heeres et al.

[11] Patent Number: 5,650,411
[45] Date of Patent: Jul. 22, 1997

[54] SUBSTITUTED AZOLONE DERIVATIVES

[75] Inventors: Jan Heeres, Vosselaar; Joseph Hector Mostmans, Antwerpen; Luc Alfons Leo Van Der Eycken, Vosselaar; Frank Christopher Odds, Schilde; Raymond Antoine Stokbroekx, Beerse; Marcel Jozef Maria Van der Aa, Turnhout, all of Belgium

[73] Assignee: Janssen Pharmaceutica N.V., Beerse, Belgium

[21] Appl. No.: 491,960

[22] PCT Filed: Feb. 9, 1994

[86] PCT No.: PCT/EP94/00380

§ 371 Date: Jul. 18, 1995

§ 102(e) Date: Jul. 18, 1995

[87] PCT Pub. No.: WO94/18978

PCT Pub. Date: Sep. 1, 1994

[30] Foreign Application Priority Data

Feb. 19, 1993 [EP] European Pat. Off. ............ 93200474

[51] Int. Cl.$^6$ .................. A61K 31/495; C07D 401/14
[52] U.S. Cl. .................. 514/252; 514/256; 514/318; 514/326; 544/238; 544/295; 544/331; 544/357; 544/364; 544/366; 544/405; 546/194; 546/210
[58] Field of Search ........................ 546/210, 194; 544/366, 364, 20.5, 331, 238, 357, 405; 514/252, 318, 326, 256

[56] References Cited

U.S. PATENT DOCUMENTS

| | | | |
|---|---|---|---|
| 4,724,239 | 2/1988 | Morgan | 514/563 |
| 4,791,111 | 12/1988 | Heeres et al. | 514/252 |
| 4,931,444 | 6/1990 | Van Wauwe et al. | 514/252 |
| 5,254,553 | 10/1993 | Heeres et al. | 514/252 |

OTHER PUBLICATIONS

H. Rautelin et al., "In Vitro Activity of Antifungal Azoles against *Helicobacter pylori*" Eur. J. Clin. Microbiol. Infect. Dis., vol. 11(3), 273–4, 1992.

D. Steinhilber et al., "Effects of Novel Antifungal Azole Derivatives on the 5-Lipoxygenase and Cyclooxygenase Pathway", Arzneim.–Forsch/Drug Res. 40(II), Nr. 11 (1990), 1260–3.

J. Ahmed et al., "Eicosainoid Synthesis and Helicobacter Pylori Associated Gastritis: Increase In Leukotriene $C_4$ Generation Associated With H. Pylori Colonization", *Prostaglandins* 44:75–86, 1992.

*Primary Examiner*—Joseph McKane
*Assistant Examiner*—Richard S. Myers, Jr.
*Attorney, Agent, or Firm*—Charles J. Metz

[57] ABSTRACT

The use for the manufacture of a medicament for treating Helicobacter-related diseases of a compound of formula

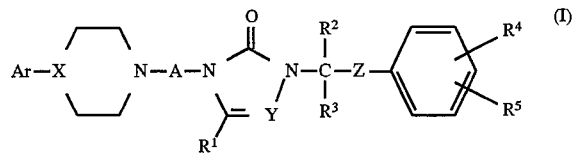

a pharmaceutically acceptable acid addition salt or a stereochemically isomeric form thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

Z is C=O or CHOH; and

Ar is phenyl optionally substituted with up to three substituents selected from hydroxy, $C_{1-4}$alkyl, $C_{1-4}$alkyloxy, halo, trifluoromethyl, tri$C_{1-4}$alkylsilyloxy, nitro, amino and cyano or pyridinyl substituted with hydroxy or $C_{1-4}$alkyloxy; and —A— is a radical of formula

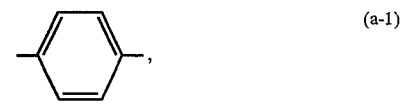 (a-1)

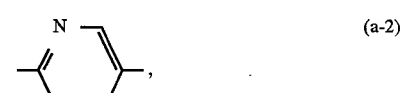

(a-2)

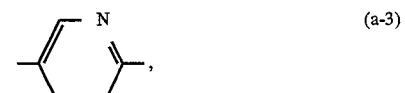

(a-3)

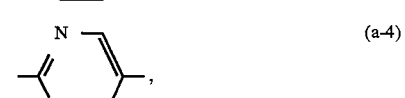

(a-4)

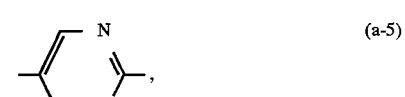

(a-5)

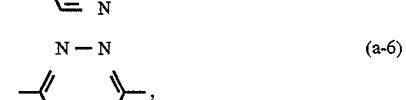

(a-6)

or

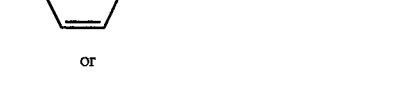 (a-7)

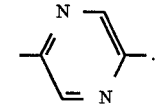

14 Claims, No Drawings

SUBSTITUTED AZOLONE DERIVATIVES

CROSS-REFERENCE TO RELATED APPLICATIONS

This application is based upon PCT application Ser. No. PCT/EP 94/00380, filed Feb. 9, 1994, which claims priority from European Application Serial No. 93.200,474.0, filed on Feb. 19, 1993.

The present invention is concerned with substituted azolone derivatives which are potent anti-Helicobacter agents and which may be used in a monotherapy in the eradication of *Helicobacter pylori* and related species.

U.S. Pat. No. 4,791,111 discloses 4-(4-phenyl-1-piperazinyl)phenols which are intermediates in the preparation of [[4-[4-(4-phenyl-1-piperazinyl)phenoxymethyl]-1,3-dioxolan-2-yl]methyl]-1H-imidazoles and 1H-1,2,4-triazoles.

In U.S. Pat. No. 4,931,444 there are described 4-(4-phenyl-1-piperazinyl)phenols having 5-lipoxygenase inhibiting activity. The present compounds are distinguished therefrom by their useful anti-Helicobacter activity.

Afflictions of the gastro-enteric tract are widespread. Modern medicine still fails to cure a lot of them, in particular those related to the presence in the gastric mucosa of the bacterium Helicobacter, e.g. chronic gastritis, duodenal ulcer and duodenal ulcer relapse. Dual therapies in the eradication of Helicobacter, comprising the separate administration of two antibiotic drugs, have not been satisfactory up till now, because of one or more of the following reasons: a low eradication rate, numerous side effects and development of resistance by Helicobacter.

Triple therapies comprising the administration of two antibiotics and a bismuth compound have been shown to be effective, but are very demanding for the patients and are also complicated by side effects.

The present invention is concerned with the use for the manufacture of a medicament for treating Helicobacter-related diseases of a compound of formula

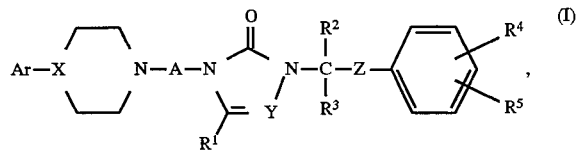

the pharmaceutically acceptable acid addition salts and the stereochemically isomeric forms thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyl or difluoromethyloxy;

Z is C=O or CHOH; and

Ar is phenyl optionally substituted with up to three substituents selected from hydroxy, $C_{1-4}$alkyl, $C_{1-4}$alkyloxy, halo, trifluoromethyl, tri$C_{1-4}$alkylsilyloxy, nitro, amino and cyano or pyridinyl substituted with hydroxy or $C_{1-4}$alkyloxy; and —A— is a radical of formula

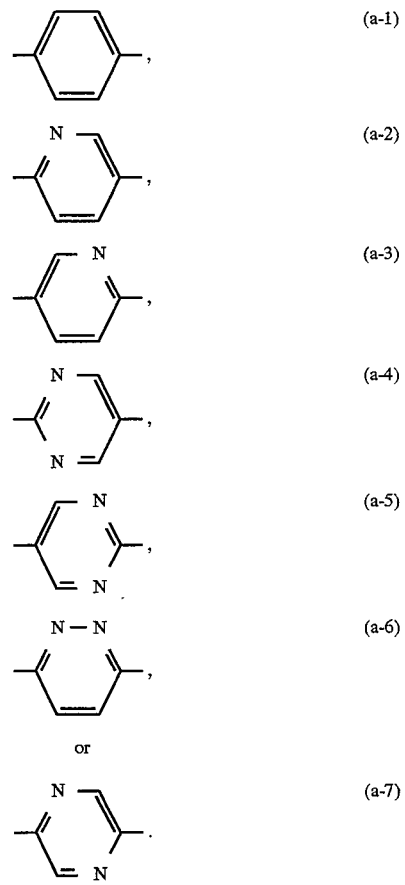

The present invention is also concerned with a method of treating subjects suffering from Helicobacter-related diseases said method comprising administering to said subjects an effective anti-Helicobacter amount of a compound of formula (I).

Further, the present invention relates to pharmaceutical compositions comprising a pharmaceutically acceptable carrier and as active ingredient an effective amount of a compound having the formula (I), a pharmaceutically acceptable acid addition salt thereof or a stereochemically isomeric form thereof, wherein X, Y, $R^1$ to $R^5$, Z, Ar and —A— are as defined in hereinabove, provided that Ar is other than 4-hydroxyphenyl, 3-$C_{1-4}$alkyl-4-hydroxyphenyl or 3,5-di$C_{1-4}$alkyl-4-hydroxyphenyl, when X=N and Q is a radical of formula (a-1).

The present invention is also concerned with a compound having the formula (I), a pharmaceutically acceptable acid addition salt thereof or a stereochemically isomeric form thereof, wherein X, Y, $R^1$ to $R^5$, Z, Ar and —A— are as defined hereinabove, provided that Ar is other than 4-hydroxyphenyl, 3-$C_{1-4}$alkyl-4-hydroxyphenyl, 3,5-di$C_{1-4}$alkyl-4-hydroxyphenyl or 4-methoxyphenyl when X=N and —A— is a radical of formula (a-1).

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl.

The term pharmaceutically acceptable acid addition salt as used hereinbefore defines the non-toxic, therapeutically active acid addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are inorganic acids such as hydrohalic acid, i.e. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanedicarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term pharmaceutically acceptable acid addition salts also comprises the solvates which the compounds of formula (I) may form, e.g. the hydrates, alcoholates and the like.

The term stereochemically isomeric forms as used hereinbefore defines the different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention. The absolute configuration of each chiral center may be indicated by the stereochemical descriptors R and S.

Some compounds of the present invention may exist in different tautomeric forms and all such tautomeric forms are intended to be included within the scope of the present invention.

Particular compounds are those compounds of formula (I) wherein $R^4$ and $R^5$ each independently are hydrogen or halo, and Ar is phenyl substituted with up to three substituents selected from hydroxy, $C_{1-4}$alkyl and $C_{1-4}$alkyloxy, or pyridinyl substituted with hydroxy or $C_{1-4}$alkyloxy.

A first group of interesting compounds are those compounds of formula (I) wherein Ar is a radical of formula

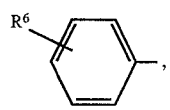
(b-1)

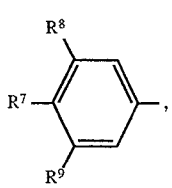
(b-2)

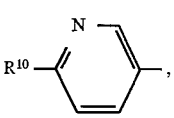
(b-3)

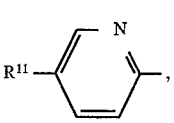
(b-4)

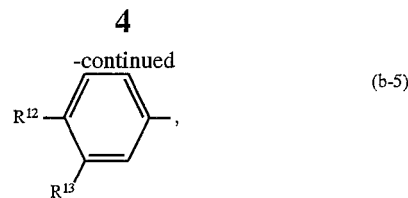
(b-5)

wherein
$R^6$, $R^7$, $R^{10}$, $R^{11}$, $R^{12}$ and $R^{13}$ each independently are hydroxy or $C_{1-4}$alkyloxy; and $R^8$ and $R^9$ are $C_{1-4}$alkyl.

A second group of interesting compounds are those compounds of formula (I) wherein X is N.

A third group of interesting compounds are those compounds of formula (I) wherein —A— is a radical of formula (a-1), (a-2) or (a-3).

A fourth group of interesting compounds are those compounds of formula (I) wherein Y is N and $R^1$ is hydrogen.

A fifth group of interesting compounds are those compounds of formula (I) wherein $R^2$ is ethyl and $R^3$ is hydrogen.

A sixth group of interesting compounds are those compounds of formula (I) wherein $R^4$ is halo substituted at the para position and $R^5$ is hydrogen.

Preferred compounds are those compounds of formula (I) wherein
$R^2$ is $C_{1-4}$alkyl;
$R^4$ is halo substituted at the para position; and
$R^1$, $R^3$ and $R^5$ are hydrogen.

More preferred compounds are those preferred compounds wherein Ar is hydroxyphenyl, methoxyphenyl, dimethoxyphenyl, $C_{1-4}$alkylphenyl, di$C_{1-4}$alkyl-phenyl or methoxypyridinyl;

—A— is a radical of formula (a-1), (a-2) or (a-3).

The most preferred compounds are

2-[1-(4-chlorobenzoyl)propyl]-2,4-dihydro-4-[6-[4-(4-methoxyphenyl)-1-piperazinyl]-3-pyridinyl]-3H-1,2,4-triazol-3-one;

2-[1-(4-chlorobenzoyl)propyl]-2,4-dihydro-4-[6-[4-(3-hydroxyphenyl)-1-piperazinyl]-3-pyridinyl]-3H-1,2,4-triazol-3-one;

2-[1-[(4-chlorophenyl)hydroxymethyl]propyl]-2,4-dihydro-4-[6-[4-(3-hydroxyphenyl)-1-piperazinyl]-3-pyridinyl]-3H-1,2,4-triazol-3-one;

2-[1-[(4-chlorophenyl)hydroxymethyl]propyl]-2,4-dihydro-4-[4-[4-(6-methoxy-3-pyridinyl)-1-piperazinyl]phenyl]-3H-1,2,4-triazol-3-one;

2-[1-(4-chlorobenzoyl)propyl]-4-[6-[4-(3-methoxyphenyl)-1-piperazinyl]-3-pyridinyl]-2,4-dihydro-3H-1,2,4-triazol-3-one;

2-[1-[(4-chlorophenyl)hydroxymethyl]propyl]-2-4-dihydro-4-[6-[4-(3-methoxyphenyl)-1-piperazinyl]-3-pyridinyl]-3H-1,2,4-triazol-3-one;

2-[1-(4-chlorobenzoyl)propyl]-4-[6-[4-(3,4-dimethoxyphenyl)-1-piperidinyl]-3-pyridinyl]-2,4-dihydro-3H-1,2,4-triazol-3-one;

2-[1-[(4-chlorophenyl)hydroxymethyl]propyl]-2,4-dihydro-4-[4-[4-(6-methoxy-2-pyridinyl)-1-piperazinyl]phenyl]-3H-1,2,4-triazol-3-one;

2-[1-[(4-chlorophenyl)hydroxymethyl]propyl]-4-[6-[4-(3,4-dimethoxyphenyl)-1-piperazinyl]-3-pyridinyl]-2,4-dihydro-3H-1,2,4-triazol-3-one; and 2-[1-(4-chlorobenzoyl)propyl]-4-[6-[4-(3,4-dimethoxyphenyl)-1-piperazinyl]-3-pyridinyl]-2,4-dihydro-3H-1,2,4-triazol-3-one, the pharmaceutically acceptable acid addition salts and the stereochemically isomeric forms thereof.

Procedures for the preparation of compounds such as the present compounds of formula (I) have been described in U.S. Pat. No. 4,791,111 and U.S. Pat. No. 4,931,444.

In particular, the compounds of formula (I) can be prepared by N-alkylating an intermediate of formula (II) with a reagent of formula (III).

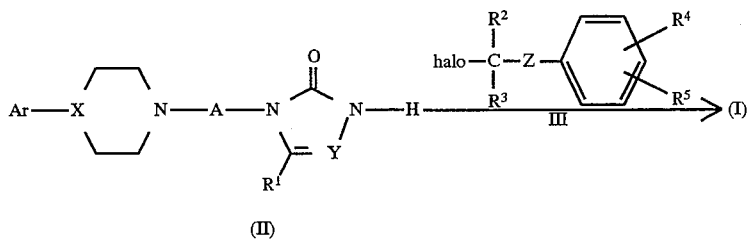

The N-alkylation reaction of (II) with (III) can conveniently be conducted by stirring and heating a mixture of the reagents in an appropriate solvent in the presence of a suitable base. Appropriate solvents are, for example dipolar aprotic solvents, e.g. N,N-dimethyl-formamide, N,N-dimethylacetamide, 1,3-dimethyl-2-imidazolidinone; aromatic solvents, e.g. benzene, methylbenzene; an ether, e.g. 1,1'-oxybisethane, tetrahydrofuran; a halogenareal hydrocarbon, e.g. dichloromethane, trichloromethane; or a mixture of such solvents.

Suitable bases are, for example, sodium bis(trimethylsilyl)amide, alkali metal and earth alkaline metal carbonates or hydrogen carbonates, e.g. sodium or potassium carbonate; or organic bases, e.g. triethylamine and the like bases.

The compounds of formula (I) can also be convened into each other following art-known procedures of functional group transformation.

For example, the compounds of formula (I) wherein Z represents C=O can be convened into the compounds of formula (I) wherein Z represents CHOH following art-known reductions. For example, said reduction can conveniently be conducted by reaction with a metal hydride or complex metal hydride, e.g. sodium borohydride, sodium cyanoborohydride and the like in water, 1-methyl-pyrrolidinone, an alcoholic medium, e.g. methanol, ethanol, or an ether, e.g. tetrahydrofuran, 1,4-dioxane; or in a mixture of such solvents.

Alternatively, said reduction can be conducted by reaction with tris(1-methylethoxy)-potassium hydroborate in a reaction-inert solvent, e.g. tetrahydrofuran.

Further, the compounds of formula (I) wherein Ar is substituted with at least one hydroxy can be prepared from the corresponding $C_{1-4}$alkyloxy derivatives by an appropriate dealkylation reaction, for example using trifluoroacetic acid, or in particular a mineral acid such as concentrated hydrohalic acid, e.g. hydrobromic acid, hydroiodic acid, optionally in admixture with a saturated solution of hydrobromic acid in glacial acetic acid; a Lewis acid, e.g. boron tribromide in a reaction-inert solvent, e.g. dichloromethane. In the instance where hydrobromic acid is used it may be advantageous to conduct said dealkylation reaction in the presence of a bromine scavenger such as, for example sodium sulfite or hydrogen sulfite.

Conversely, the compounds of formula (I), wherein Ar is substituted with at least one $C_{1-4}$alkyloxy can be prepared by alkylating the corresponding hydroxy derivatives with an appropriate alkylating reagent, e.g. dimethylsulfate and the like. Optionally, said alkylation may be carried out by applying art-known conditions of phase transfer catalysis reactions. Said conditions comprise stirring the reactants with an appropriate base, e.g. sodium hydroxide in a reaction-inert solvent, e.g. dichloromethane, in the presence of a suitable phase transfer catalyst, e.g. benzyltriethylammonium chloride and the like.

The compounds of formula (I) wherein Ar is substituted with a hydroxy group may be converted in the corresponding tri$C_{1-4}$alkylsilyloxy compound upon reaction with tri$C_{1-4}$alkyl-Si-L$^7$, L$^7$ being a reactive leaving group, e.g. halo, in a reaction-inert solvent, e.g. pyridine, dichloromethane.

Conversely, the compounds of formula (I) wherein Ar is substituted with a tri$C_{1-4}$alkylsilyloxy group may be converted in the corresponding hydroxy compound upon reaction with a fluoride such as (n-$C_4H_9$)$_4$N$^+$F$^-$ in a reaction-inert solvent, e.g. tetrahydrofuran, dichloromethane.

Finally, pure isomeric forms of the compounds of formula (I) can be separated from the mixture by conventional separation methods. In particular, the enantiomers may be separated by column chromatography using a chiral stationary phase such as a suitably derivatized cellulose, for example, tri(dimethylcarbamoyl)cellulose (Chiralcel OD®) and similar chiral stationary phases.

In all foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds.

The intermediates of formula (II) can be prepared by cyclizing an intermediate of formula (IV) with a reagent of formula (V) or a derivative thereof.

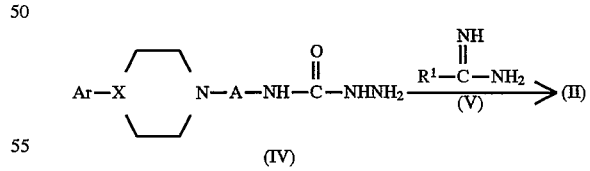

An appropriate reaction-inert solvent for the above cyclization reaction is, for example, a dipolar aprotic solvent, e.g. N,N-dimethylformamide, dimethyl sulfoxide and the like, or an alcohol, e.g. ethanol, 1-butanol and the like.

The intermediates of formula (IV) can be prepared by reacting an intermediate of formula (VI) with hydrazine or a derivative thereof in a reaction-inert solvent, e.g. 1,4-dioxane and the like.

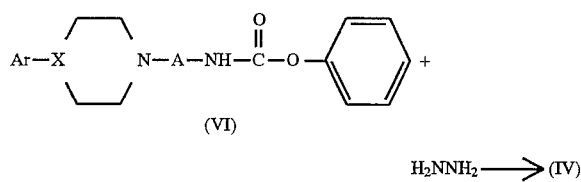
(VI)

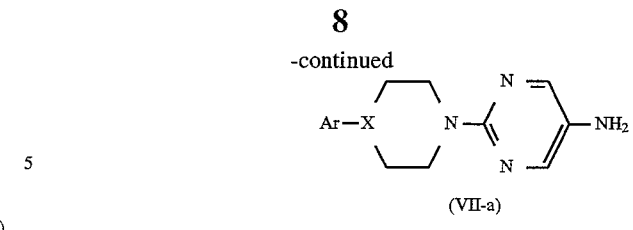
(VII-a)

H₂NNH₂ ⟶ (IV)

The preparation of the intermediates of formula (X) as described above is conveniently conducted in a reaction-inert solvent, e.g. 1-propanol, methanol or a mixture thereof, preferably in the presence of a base, e.g. sodium methoxide. The preparation of the intermediates (VII-a) from the intermediates (X) may be conducted in the presence of a base, e.g. sodium hydroxide and the like.

The intermediates of formula (VI) can be prepared by reacting an intermediate of formula (VII) with phenyl chloroformate in a reaction-inert solvent, such as, for example, a dipolar aprotic solvent, e.g. N,N-dimethylformamide, N,N-dimethylacetamide, an aromatic solvent, e.g. pyridine, or a halogenated hydrocarbon, e.g. dichloromethane and the like, or a mixture of such solvents.

The intermediates of formula (VIII) can be prepared by reacting the intermediates of formula (XI) with a reagent of formula (XII) wherein L is a reactive leaving group, e.g. halo, in a reaction-inert solvent, e.g. N,N-dimethylacetamide, dimethyl sulfoxide, N,N-dimethylformamide, bis(2-methoxyethyl)ether, 3-methoxy-1-propanol and the like, preferably in the presence of a base, e.g. potassium carbonate and the like.

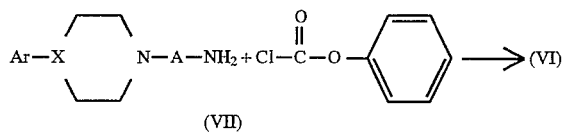
(VII)

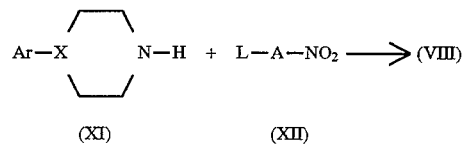
(XI)  (XII)

The intermediates of formula (VII) can be prepared by reducing the corresponding nitro compound of formula (VIII) following art-known procedures.

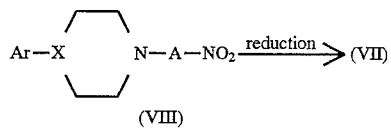
(VIII)

The intermediates of formula (XI) wherein X is N, said intermediates being represented by the formula (XI-a), can be prepared by reacting the intermediates of formula (XIII) with a reagent of formula (XIV) wherein $L^1$ and $L^2$ are reactive leaving groups, e.g. halo, in a reaction-inert solvent, e.g. 1-butanol, hexanol and the like, preferably in the presence of a base, e.g. potassium carbonate and optionally in the presence of a small amount of potassium iodide.

Suitable art-known reduction procedures are, for example, catalytic hydrogenation in a suitable solvent, e.g. methanol, tetrahydrofuran, N,N-dimethylformamide, in the presence of hydrogen and an appropriate catalyst, e.g. palladium-on-charcoal, Raney nickel and the like, optionally in the presence of thiophene.

Alternatively, the intermediates of formula (VII) can be prepared by reacting the compounds of formula (VIII) with hydrazine or a derivative thereof in a reaction-inert solvent, e.g. methanol, in the presence of a catalyst, e.g. Raney nickel.

Further, the intermediates of formula (VII) wherein —A— is a radical of formula (a-4) can be prepared by reacting the intermediates of formula (IX) or a derivative thereof according to the following reaction procedure.

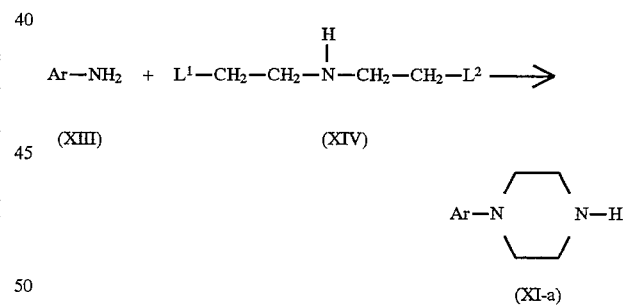
(XIII)  (XIV)

(XI-a)

Optionally, the above reaction may be conducted using an N-protected intermediate (XIV), e.g. the tosyl derivative thereof. After reaction with intermediate (XIII), the protective group may be removed upon treatment with a diluted acid, e.g. sulfuric acid.

Alternatively, the intermediates of formula (XI-a) wherein Ar is substituted with methoxy can be prepared by the following reaction procedure.

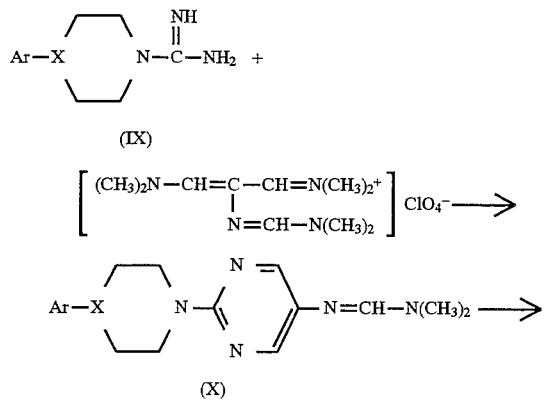

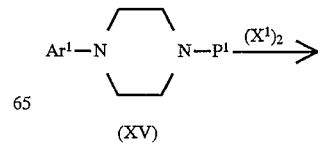
(XV)

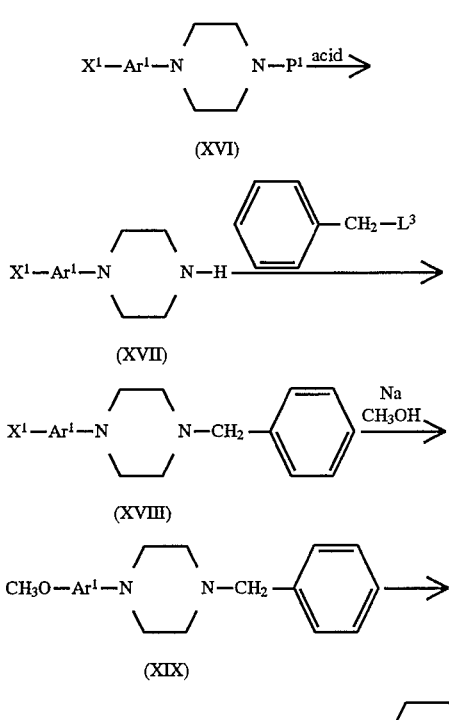

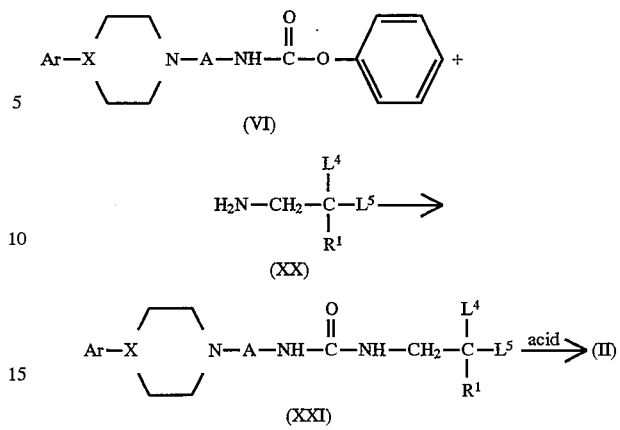

Ar¹ as used hereinabove represents phenyl of pyridinyl, P¹ represents a protective group, e.g. $C_{1-4}$alkyloxycarbonyl, X¹ represents halo, in particular bromo or iodo, and L³ represents a reactive leaving group, e.g. halo. The preparation of the intermediates of formula (XVI) is preferably conducted in a reaction-inert solvent, e.g. carbon disulfide.

The protective group in the intermediates of formula (XVI) may be removed upon treatment with an acid, e.g. hydrobromic acid. The preparation of the intermediates of formula (XVIII) preferably is conducted in a reaction-inert solvent, e.g. dimethyl-benzene, optionally in the presence of a base, e.g. sodium hydrogen carbonate. Further, the preparation of the intermediates of formula (XIX) as described above may optionally be conducted in the presence of a catalyst, e.g. copper(I)iodide and the like, optionally under nitrogen atmosphere. Finally, the benzyl moiety in the intermediates of formula (XIX) may be removed upon catalytic hydrogenation following an-known procedures. Alternatively, the intermediate of formula (XVI) may be prepared from the corresponding aniline compound following an-known procedures.

In order to prepare the intermediates of formula (II), an intermediate of formula (VI) can be reacted with a reagent of formula (XX) wherein L⁴ and L⁵ are reactive leaving groups, e.g. $C_{1-4}$alkyloxy, in a reaction-inert solvent, e.g. 1,4-dioxane and the like, yielding an intermediate of formula (XXI). The latter intermediate may then be cyclized upon treatment with an acid, e.g. hydrochloric acid.

In a further alternative, the intermediates of formula (II) can be prepared by first reacting an intermediate of formula (VI) with a reagent of formula (XXII) or a derivative thereof in a reaction-inert solvent, e.g. 1,4-dioxane, optionally in the presence of a base, e.g. N,N-dimethyl-4-pyridinamine to yield an intermediate of formula (XXIII). The latter intermediate may then be cyclized upon treatment with an acid, e.g. formic acid.

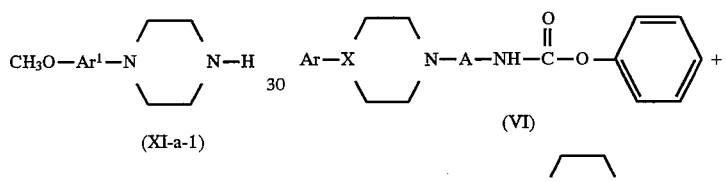

The intermediates of formula (II) can also be prepared by reacting an intermediate of formula (VII) with a reagent of formula (XXIV) wherein R⁶ is $C_{1-6}$alkyl, e.g. methyl or ethyl, and L⁶ represents a reactive leaving group, e.g. $C_{1-6}$alkyloxy or di($C_{1-6}$alkyl)-amino, e.g. methoxy, ethoxy or dimethylamino, in a reaction-inert solvent, e.g. tetrahydrothiophene 1,1-dioxide and the like.

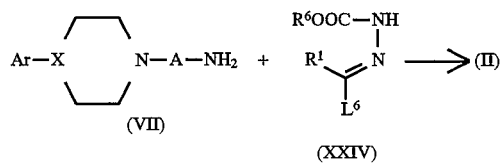

The compounds of formula (I), the pharmaceutically acceptable acid addition salts and the stereochemically isomeric forms thereof display useful pharmacological activity against Helicobacter species; e.g. *Helicobacter pylori, Helicobacter mustelae, Helicobacter felis* and the like, in particular *Helicobacter priori*.

Particularly important in this context is the finding that the subject compounds show inhibitory activity against the growth of Helicobacter as well as bactericidal activity against said bacteria. The bactericidal effect on Helicobacter was determined with suspension cultures by means of a procedure described in Antimicrob. Agents Chemother., 1991, vol. 35, pp. 869–872.

An interesting feature of the present compounds relates to their highly specific activity against Helicobacter. The compounds of formula (I) were found to show no inhibitory activity against any of the following species: *Campylobactor jejuni, Campylobacter coli, Campylobacter fetus, Campylobacter sputorum, Vibrio spp., Staphylococcus aureus* and *Escherichia coli*, tested at concentrations up to $10^{-5}$M.

An important asset of the present compounds is their sustained activity against *H. pylori* at pH below the normal neutral pH. Activity at a low pH in vitro may indicate that a compound is not adversely affected by the acidic environment of the stomach in vivo.

Consequently, the subject compounds are considered to be valuable therapeutical drugs for treating warm-blooded animals, particularly humans, suffering from Helicobacter related diseases or afflictions. Examples of said diseases or afflictions are gastritis, stomach ulcers, duodenal ulcers and gastric cancer.

In view of their useful anti-Helicobacter properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carders are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

When the pharmaceutical composition takes the form of an aqueous solution, those compounds of formula (I) which display low solubility may be formulated as a salt form, or a co-solvent may be added which is water-miscible and physiologically acceptable, e.g. dimethylsulfoxide and the like, or the compounds of formula (I) may be solubilized with a suitable carrier, e.g. a cyclodextrin (CD) or in particular a cyclodextrin derivative such as the cyclodextrin derivates described in U.S. Pat. No. 3,459,731, EP-A-149, 197 (Jul. 24, 1985), EP-A-197,571 (Oct. 15, 1986), U.S. Pat. No. 4,535,152 or WO 90/12035 (Oct. 18, 1990). Typically such derivatives comprise α-, β- or γ-CD wherein one or more hydroxyl groups are substituted with $C_{1-6}$alkyl, particularly methyl, ethyl or isopropyl; hydroxy$C_{1-6}$alkyl, particularly hydroxyethyl, hydroxypropyl or hydroxy-butyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl; carboxy$C_{1-6}$alkyloxy$C_{1-6}$alkyl, particularly carboxymethoxypropyl or carboxyethoxypropyl or $C_{1-6}$alkyl-carbonyloxy$C_{1-6}$alkyl, particularly 2-acetyloxypropyl. Especially noteworthy as complexants and/or solubilizers are β-CD, 2,6-dimethyl-β-CD and in particular 2-hydroxypropyl-β-CD, 2-hydroxyethyl-β-CD, 2-hydroxyethyl-γ-CD, 2-hydroxypropyl-γ-CD and (2-carboxymethoxy)propyl-β-CD. In the aforementioned cyclodextrin derivatives, the DS (degree of substitution, i.e. the average number of substituted hydroxy functions per glucose unit) is preferably in the range of 0.125 to 3, in particular 0.2 to 2, or 0.2 to 1.5. More preferably the DS ranges from about 0.2 to about 0.7, in particular from about 0.35 to about 0.5 and most particularly is about 0.4. The MS (molar degree of substitution, i.e. the average number of moles of the substituting agent per glucose unit) is in the range of 0.125 to 10, in particular of 0.3 to 3, or 0.3 to 1.5. More preferably the MS ranges from about 0.3 to about 0.8, in particular from about 0.35 to about 0.5 and most particularly is about 0.4. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. The amount of the cyclodextrin or ether derivative thereof in the final composition generally ranges from about 1% to about 40%, particularly from 2.5% to 25% and more particularly from 5 % to 20%.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Helicobacter related diseases it is evident that the present invention provides a method of treating warm-blooded animals, in particular humans, suffering from Helicobacter related diseases, said method comprising the systemic administration of a pharmaceutically effective amount of a compound of formula (I), a pharmaceutically acceptable acid addition salt thereof or a stereochemically isomeric form thereof, in admixture with a pharmaceutical carrier. In general it is contemplated that an effective daily amount would be from 0.05 mg/kg to 20 mg/kg body weight, preferably from 0.1 mg/kg to 10 mg/kg body weight and more preferably form 0.5 mg/kg to 5 mg/kg body weight. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

Optionally, other active compounds used for the eradication of Helicobacter can be administered in combination with the compounds of the present invention. The administration may occur separately (i.e. simultaneously, concurrently or consecutively) or the different drugs may be combined in one dosage form. The preferred compounds for a combination therapy are bismuth compounds, e.g. bismuth subcitrate, bismuth subsalicylate, and the like, and proton pump inhibitors, e.g. omeprazole, lansoprazole, and the like.

EXPERIMENTAL PART

A. Preparation of the Intermediates

Example 1 a) A mixture of 1-(4-methoxyphenyl)piperazine dihydrochloride (0.050 mol), 1-chloro-4-nitrobenzene (0.050 mol) and potassium carbonate (10.0 g) in N,N-dimethylformamide (100 ml) was stirred and refluxed overnight. The reaction mixture was diluted with water and extracted twice with trichloromethane. The organic layers were combined, dried (MgSO₄), filtered and evaporated in vacuum. The residue was successively triturated in 4-methyl-2-pentanone and recrystallized from 1,4-dioxane. The product was filtered off and dried, yielding 10.5 g (67%) of 1-(4-methoxyphenyl)-4-(4-nitrophenyl)-piperazine; mp. 195.1° C. (interm. 1).

b) A mixture of intermediate (1) (0.038 mol) in methanol (250 ml) and tetrahydrofuran (250 ml) was hydrogenated at normal pressure and room temperature with palladium on activated carbon 10% (2 g) as a catalyst. After uptake of hydrogen (3 equiv), the catalyst was filtered off and rinsed with N,N-dimethylacetamide. The combined filtrates were poured into water. The precipitate was filtered off and recrystallized from 1-butanol. The product was filtered off and dried, yielding 8 g (74%) 4-[4-(4-methoxyphenyl)-1-piperazinyl]benzenamine; mp. 191.8° C. (interm. 2).

c) A mixture of intermediate (2) (0.021 mol) and phenyl chloroformate (0.023 mol) in pyridine (75 ml) and dichloromethane (75 ml) was stirred and heated until complete dissolution. Stirring was continued for 30 minutes at room temperature. The reaction mixture was poured into a mixture of 500 ml of water and 300 ml of 2,2'-oxybispropane. After stirring, the precipitate was filtered off, dried and recrystallized from 1-butanol. The product was filtered off and dried, yielding 5.2 g (61%) of phenyl [4-[4-(4-methoxyphenyl)-1-piperazinyl]phenyl]carbamate; mp. 204.5° C. (interm. 3).

d) A mixture of intermediate (3) (0.008 mol) in hydrazine monohydrate (50 ml) and 1,4-dioxane (100 ml) was stirred and refluxed for 3 hours. After cooling, the reaction mixture was poured into water. The precipitate was filtered off and recrystallized from N,N-dimethylformamide. The product was filtered off and dried, yielding 1.7 g (62%) of N-[4-[4-(4-methoxyphenyl)-1-piperazinyl]phenyl] hydrazinecarboxamide; mp. >300° C. (interm. 4).

e) A mixture of intermediate (4) (0.001 mol) and methanimidamide acetate (0.029 mol) in dimethyl sulfoxide (10 ml) was heated for 2 hours at 160° C. After cooling, the reaction mixture was poured into a mixture of 4-methyl-2-pentanone and 2,2'-oxybispropane. The precipitate was filtered off and treated with activated charcoal in N,N-dimethylformamide. After filtration, the product was allowed to crystallize. The product was filtered off and dried, yielding 1 g (28%) of 2,4-dihydro-4-[4-[4-(4-methoxyphenyl)-1-piperazinyl]phenyl]-3H-1,2,4-triazol-3-one; mp>300° C. (interm. 5).

Example 2

A mixture of intermediate (4) (0.15mol) and ethanimidamide hydrochloride (0.56 mol) in N,N-dimethylformamide (150 ml) was stirred for 3 hours at 130° C. After cooling, the reaction mixture was poured into water. The precipitate was filtered off, washed with water and CH₃OH and crystallized from N,N-dimethylformamide. The product was filtered off and recrystallized from 1,4-dioxane, yielding 19.5 g (33.3%) of 2,4-dihydro-4-[4-[4-(4-methoxyphenyl)-1-piperazinyl] phenyl]-5-methyl-3H-1,2,4-triazol-4-one; mp. 298.4° C. (interm. 6).

Example 3 a) A mixture of 10 g of intermediate (3), 3 g of 2,2-dimethoxyethanamine and 100 ml of 1,4-dioxane was stirred and refluxed for 6 hours. The reaction mixture was cooled. The precipitated product was filtered off, washed with 1,4-dioxane and purified by column-chromatography over silica gel using a mixture of trichloromethane and methanol (99:1) as eluent. The pure fractions were collected and the eluent was evaporated. The residue was crystallized from 1,4-dioxane, yielding 3.9 g of N-(2,2-dimethoxyethyl)-N'-[4-[4-(4-methoxyphenyl)-1-piperazinyl]phenyl]urea; mp. 225° C. (interm. 7).

b) A mixture of 70 g of intermediate (7), 84 g of concentrated hydrochloric acid, 300 ml of water and 350 ml of methanol was stirred and heated for 30 minutes at 80° C. The reaction mixture was allowed to cool to room temperature while the product was allowed to crystallize. It was filtered off, washed with water and dried, yielding 24.5 g (37%) of 1,3-dihydro-1-[4-[4-(4-methoxyphenyl)-1-piperazinyl]phenyl]-2H-imidazol-2-one monohydrochloride monohydrate; mp. 256.2° C. (interm. 8).

Example 4 a) A mixture of 4.4 g of intermediate (3), 1.6 g of 2-aminomethyl-2-methyl-1,3-dioxolane monohydrate, 100 ml of 1,4 dioxane, 1 g of N,N-dimethyl-4-pyridinamine and 4 g of N,N-diethylethanamine were stirred and refluxed for 3 hours. Water was added and the mixture was cooled and allowed to crystallize. The product was filtered off, washed with water and 2-propanol and dried, yielding 3.8 g (89.1%) of N-[4-[4-(4-methoxyphenyl)-1-piperazinyl]phenyl]-N'-[ (2-methyl-1,3-dioxolane-2-yl)methyl]urea (interm. 9)

b) A mixture of 3.3 g of intermediate (9) and 100 ml of formic acid was stirred for 1 hour at 70° C. The reaction mixture was evaporated and the residue was neutralized with a sodium hydrogen carbonate solution. 4-Methyl-2-pentanone was added. The whole was stirred and the product was filtered off. The residue was washed with water and 4-methyl-2-pentanone. The product was recrystallized from N,N-dimethylformamide, yielding 2.0 g (71.3%) of 1,3-dihydro-1-[4-[4-(4-methoxyphenyl)-1-piperazinyl]-phenyl]-5-methyl-2H-imidazol-2-one; mp. >300° C. (interm. 10).

Example 5 a) To a stirred and cooled (<10° C.) mixture of 150 g of ethyl 4-(2-pyridinyl)-1-piperazinecarboxylate and 1535 ml of carbon sulfide were added dropwise 32.8 ml of bromine. Upon completion, stirring was continued for 18 hours, while meantime the mixture was allowed to reach room temperature. At a temperature below 20° C., there was added a solution of 70 g of sodium hydroxide solution 10N in 300 ml of water. After stirring for 3 hours at room temperature, the layers were separated. The aqueous phase was extracted twice with trichloromethane. The combined organic phases were washed with water, dried, filtered and evaporated. 46 ml of benzene were added to the residue and the whole was evaporated again. Upon standing for 48 hours, the product was solidified. The oily phase was decanted and the solid product was crystallized twice from 2,2'-oxybispropane at 10° C. It was filtered off and dried, yielding 100 g of ethyl 4-(5-bromo-2-pyridinyl)-1-piperazinecarboxylate; mp. 68° C. (interm. 11).

b) A mixture of 18 g of intermediate (11) and 50 ml of an aqueous hydrobromic acid solution 48% was stirred and refluxed for 2 hours. The reaction mixture was cooled and evaporated. The solid residue was dissolved in water and the solution was alkalized with a sodium hydroxide solution 10N at a temperature below 20° C. The product was extracted twice with trichloromethane. The combined extracts were washed with water, dried, filtered and evaporated. The solid residue was dried at room temperature at the air, yielding 12.3 g of 1-(5-bromo-2-pyridinyl)piperazine; mp. 70.6° C. (interm. 12).

c) A mixture of 9.7 g of intermediate (12), 3.7 g of sodium hydrogen carbonate and 40 ml of dimethylbenzene was stirred and heated to reflux. Then there was added dropwise a solution 4.8 ml (bromomethyl)benzene in 10 ml dimethylbenzene at reflux. Upon completion, stirring at reflux was continued for 4 hours. The reaction mixture was cooled to room temperature, 75 ml of water were added and the layers were separated. The aqueous phase was extracted with trichloromethane. The combined organic phases were dried, filtered and evaporated in vacuo. The residue was crystallized from 2,2'-oxybispropane at 4° C. The product was sucked off and dried, yielding 6.5 g of 1-(5-bromo-2-pyridinyl)-4-(phenylmethyl)piperazine; mp. 100° C. (interm. 13).

d) Sodium (0.6 mol) was added portionwise to methanol (500 ml) upon stirring and the mixture was stirred till all the product reacted. Intermediate (13) (0.15 mol), cuprous iodide (0. 15 mol) and N,N-dimethylformamide (500 ml) were added and the mixture was stirred and refluxed for 48 hours. The mixture was filtered off and evaporated. The residue was purified by column chromatography over silica gel (eluent: EtOAc/hexane/CH$_2$Cl$_2$ 1½). The pure fractions were collected and evaporated, yielding 33.5 g (79%) of 1-(5-methoxy-2-pyridinyl)-4-(phenylmethyl)piperazine (interm 14).

e) Intermediate (14) (0.11 mol) in methanol (250 ml) was hydrogenated with palladium-on-activated charcoal (10%) (7 g) as a catalyst at 50° C. After uptake of hydrogen (2 eq), the catalyst was filtered off and the tiltrate was evaporated, yielding 19.3 g (88%) of 1-(5-methoxy-2-pyridinyl) piperazine (interm. 15).

f) A mixture of intermediate (15) (0.094 mol) and N,N-dimethylacetamide (0.15 mol) in potassium carbonate (1 00 ml) was stirred at room temperature. 1-Fluoro-4-nitrobenzene (0.12 mol) was added dropwise and the mixture was stirred at room temperature overnight. The mixture was poured into water, the precipitate was filtered off and dried, yielding 20.6 g (70%) of product. A sample (1 g) was crystallized from 2-propanol and purified by column chromatography over silica gel (eluent: CH$_2$Cl$_2$/CH$_3$CN/CH$_3$OH 97/2/0.25). The pure fractions were collected and evaporated. The residue (0.8 g) was triturated with 2,2'-oxybispropane, yielding 0.8 g of 1-(5-methoxy-2-pyridinyl)-4-(4-nitrophenyl)piperazine; mp. 160.2° C. (interm. 16).

g) Intermediate (16) (0.062 mol) in N,N-dimethylformamide (500 ml) was hydrogenated with Raney nickel (6 g) as a catalyst at 50° C. overnight. After uptake of hydrogen (3 eq), the catalyst was filtered off and the filtrate was evaporated. The residue was used without further purification, yielding 17.6 g (100%) of 4-[4-(5-methoxy-2-pyridinyl)-1-piperazinyl]benzenamine (interm. 17).

h) Phenyl chloroformate (0.11 mol) was added dropwise to a stirring mixture of intermediate (17) (0.062 mol) in N,N-dimethylformamide (100 ml) on a waterbath and the mixture was stirred overnight. Water was added, the precipitate was filtered off and dried, yielding 25 g (99%) of phenyl [4-[4-(5-methoxy-2-pyridinyl)-1-piperazinyl]-phenyl]carbamate (interm. 18).

i) A mixture of intermediate (18) (0.062 mol) and hydrazine monohydrate (0.62 mol) in 1,4-dioxane (500 ml) was stirred at 50° C. for 48 hours. The mixture was poured into water, the precipitate was filtered off and dried, yielding 15 g (71%) of N-[4-[4-(5-methoxy-2-pyridinyl)-1-piperazinyl] phenyl]hydrazinecarboxamide (interm. 19).

j) A mixture of intermediate (19) (0.044 mol) and methanimidamide acetate (0.22 mol) in 1-butanol (300 ml) was stirred and refluxed overnight. The mixture was poured into water and extracted with CH$_2$Cl$_2$. The organic layer was dried, filtered off and evaporated. The residue was purified by column chromatography over silica gel (eluent: CH$_2$Cl$_2$/CH$_3$OH 95/5). The pure fractions were collected and evaporated, yielding 3.2 g of 2,4-dihydro-4-[4-[4-(5-methoxy-2-pyridinyl)-1-piperazinyl]phenyl]-3H-1,2,4-triazol-3-one (interm. 20).

Example 6 a) A mixture of 36 g of 1-(4-methoxyphenyl)piperazine dihydrochloride, 22 g of 2-chloro-5-nitropyridine, 58 g of potassium carbonate and 227 ml of dimethyl sulfoxide was stirred overnight at 140° C. The reaction mixture was cooled and poured onto water. The precipitated product was filtered off, washed with water and dissolved in dichloromethane. The solution was treated with activated charcoal. The latter is filtered off and the filtrate was evaporated. The residue was triturated in 2-propanol. The product was filtered off and crystallized from 1-butanol, yielding 24.5 g of 1-(4-methoxyphenyl)-4-(5-nitro-2-pyridinyl)piperazine; mp. 170° C. (interm. 21).

b) To a mixture of 36 ml of hydrazine monohydrate, 4.0 g of Raney nickel and 1000 ml of methanol in reflux, were added portionwise over 25 minutes 35.0 g of intermediate (21). After stirring for 35 minutes at reflux temperature, an additional 11 ml of hydrazine monohydrate was added. The reflux was continued for 10 minutes. An additional 0.5 g of Raney nickel was added and the mixture was refluxed for 15 minutes. The reaction mixture was cooled, the catalyst was filtered off and the tiltrate was evaporated, yielding 33.57 g of 6-[4-(4-methoxyphenyl)-1-piperazinyl]-3-pyridinamine as crude product; mp. 144°–147° C. (interm. 22).

c) A mixture of 31.21 g intermediate (22), 38.40 g of (1-ethoxyethylidene) hydrazine-carboxylic acid ethyl ester and 10 ml of tetrahydrothiophene 1,1-dioxide was heated in an oil bath of 154°–158° C. for 17 hours. After cooling, 150 ml of 2-propanol was added and the mixture was filtered. The residue was recrystallized from a mixture of acetonitrile and N,N-dimethylformamide (90/10). The residue was purified by flash chromatography (eluent; CH$_2$Cl$_2$/CH$_3$OH (NH$_4$OH 10%) 98:2→96:4). The eluent of the desired fraction was evaporated and the residue was recrystallized from a mixture of N,N-dimethylformamide and acetonitrile, yielding 2,4-dihydro-4-[6-[4-(4-methoxyphenyl)-1-piperazinyl]-3-pyridinyl]-5-methyl-3H-1,2,4-triazol-3-one; mp. 251°–252° C. (interm. 23).

Example 7 a) To a mixture of 20 g of 4-(4-methoxyphenyl)-1-piperazinecarboximidamide and 21 g of N-[3-

(dimethylamino)methylene]amino]-2-propenylidene]-N-methylmethanaminium perchlorate in 200 ml of 1-propanol were added dropwise 70 ml of a solution of sodium methoxide in methanol (1M). After stirring for 2 hours there were added dropwise again 70 ml of a solution of sodium methoxide in methanol (1M). Then the mixture was stirred and refluxed for 2 hours. After cooling, the reaction mixture was evaporated and the residue was purified by column chromatography (eluent: $CH_2Cl_2/CH_3OH$ 97:3). The eluent of the desired fraction was evaporated, yielding 15 g (62.5%) of N-[(dimethylamino)methylene]-2-[4-(4-methoxyphenyl)-1-piperazinyl]-5-pyrimidinamine (interm. 24);

b) A mixture of 10 g of intermediate (24) and 150 ml of sulfuric acid (0.2M) was stirred and refluxed for 4 hours. After cooling, the mixture was neutralized with a solution of potassium carbonate in water. The product was extracted with dichloromethane and the extract was washed with water, dried, filtered and evaporated. The residue was purified by column chromatography (eluent: $CH_2Cl_2/CH_3OH$ 98:2). The eluent of the desired fraction was evaporated and the residue was crystallized from ethyl acetate. The product was filtered off and dried in vacuo at 50° C., yielding 3.5 g (40.9%) of 2-[4-(4-methoxyphenyl)-1-piperazinyl]-5-pyrimidinamine; mp. 157.1° C. (interm. 25).

c) To a stirred mixture of 10 g of intermediate (25) in 100 ml of N,N-dimethylacetamide on an ice-bath was added dropwise 4.8 ml of phenyl chloroformate. After stirring for 2 hours at room temperature, the reaction mixture was poured into ice-water. The precipitate was filtered off and dried in vacuo at 50° C., yielding 7.7 g (54.3%) of phenyl [2-[4-(4-methoxyphenyl)-1-piperazinyl]-5-pyrimidinyl]carbamate (interm. 26).

d) A mixture of 7.7 g of intermediate (26), 10 ml hydrazine monohydrate and 60 ml of 1,4-dioxane was stirred overnight at room temperature. The reaction mixture was poured into water and the precipitate was filtered off and washed with methanol. The product was purified by column chromatography (eluent: $CH_2Cl_2/CH_3OH$ 96:4). The eluent of the desired fraction was evaporated and the residue was stirred in methanol, filtered off and dried in vacuo at 75° C., yielding 1.5 g (23.0%) of N-[2-[4-(4-methoxyphenyl)-1-piperazinyl]-5-pyridinyl]hydrazinecarboxamide; mp. >300° C. (decomp.) (interm. 27).

e) A mixture of 3 g of intermediate (27), 3.7 g of methanimidamide acetate and 35 ml of 1-butanol was stirred and refluxed overnight. The reaction mixture was cooled and the precipitate was filtered off, washed with 2,2'-oxybispropane and dried in vacuo at 70° C., yielding 2.0 g (62.9%) of 2,4-dihydro-4-[2-[4-(4-methoxyphenyl)-1-piperazinyl]-5-pyrimidinyl]-3H-1,2,4-triazol-3-one; mp. 272.5° C. (interm. 28).

Example 8 a) A mixture of 6-methoxy-3-pyridinamine (0.2 mol) and 2-chloro-N-(2-chloroethyl)-ethanamine hydrochloride (0.3 mol) in 2-butanol (500 ml) was stirred and refluxed. Potassium carbonate (0.7 mol) was added portionwise (20 g/h), the mixture was refluxed for 48 hours, an additional amount of potassium carbonate (30 g) was added and the mixture was stirred for 48 hours. The mixture was poured into water, extracted with $CH_2Cl_2$ and separated. The organic layer was dried, filtered and evaporated, yielding 38 g (98%) of 1-(6-methoxy-3-pyridinyl)piperazine (interm. 29).

b) A mixture of intermediate (29) (0.2 mol) and potassium carbonate (0.5 mol) in N,N-dimethylacetamide (500 ml) was stirred at room temperature. 1-Fluoro-4-nitrobenzene (0.24 mol) was added dropwise and the mixture was stirred overnight. The mixture was poured into water and the precipitate was filtered off, yielding 16.3 g (30%) of 1-(6-methoxy-3-pyridinyl)-4-(4-nitrophenyl)piperazine (interm. 30).

In a similar way but using bis(2-methoxyethyl)ether as a solvent there were prepared:
1-(3-methoxyphenyl)-4-(5-nitro-2-pyridinyl)piperazine (interm. 31 );
2-[4-(3-methoxyphenyl)-1-piperidinyl]-5-nitropyridine; mp. 147.3° C. (interm. 32); and
1-(2-methoxyphenyl)-4-(5-nitro-2-pyridinyl)piperazine; mp. 130.8° C. (interm. 33).

c) Intermediate (30) (0.042 mol) in N,N-dimethylformamide (500 ml) was hydrogenated with Raney nickel (6 g) as a catalyst at 50° C. overnight. After uptake of hydrogen (3 eq.), the catalyst was filtered off and the filtrate was evaporated. The residue was triturated with 2,2'-oxybispropane, yielding 11.5 g (96%) of product. A sample (0.5 g) was recrystallized from 2,2'-oxybispropane, yielding 0.3 g of 4-[4-(6-methoxy-3-pyridinyl)-1-piperazinyl]benzenamine mp. 150.0° C. (interm. 34).

In a similar way there were prepared: p0 6-[4-(3-methoxyphenyl)-1-piperazinyl]-3-pyridinamine; mp. 110.6° C. (interm. 35);
6-[4-(3-methoxyphenyl)-1-piperidinyl]-3-pyridinamine; mp. 124.9° C. (interm. 36); and
6-[4-(2-methoxyphenyl)-1-piperazinyl]-3-pyridinamine (interm. 37).

d) A mixture of intermediate (34) (0.025 mol) and ethyl 2-[(dimethylamino)methylene]-hydrazinecarboxylate (0.075 mol) in tetrahydrothiophene 1,1-dioxide (10 ml) was stirred at 150° C. for 5 hours. A mixture of 2-propanol/2,2'-oxybispropane 50/50 was added. The precipitate was filtered off, washed and dried, yielding 6.5 g (74%) of 2,4-dihydro-4-[4-[4-(6-methoxy-3-pyridinyl)-1-piperazinyl]phenyl]-3H-1,2,4-triazol-3-one (interm. 38).

In a similar way there were prepared:
2,4-dihydro-4-[6-[4- (3-methoxyphenyl)-1-piperazinyl]-3-pyridinyl]-3H-1,2,4-triazol-3-one; mp. 242.6° C. (interm. 39);
2,4-dihydro-4-[6-[4-(3-methoxyphenyl)-1-piperidinyl]-3-pyridinyl]-3H-1,2,4-triazol-3-one (interm. 40); and
2,4-dihydro-4-[6-[4-(2-methoxyphenyl)-1-piperazinyl]-3-pyridinyl]-3H-1,2,4-triazol-3-one (interm. 41).

Example 9 a) A mixture of 10 g of 4-methoxy-3,5-dimethylbenzenamine hydrochloride, 19.9 g of N,N-bis(2-chloroethyl)-4-methylbenzenesulfonamide, 16.8 g of sodium carbonate, 0.5 g of potassium iodide and 100 ml of cyclohexanol was stirred overnight at 150°–160° C. After cooling, the reaction mixture was poured into water. The product was extracted with dichloromethane. The extract was washed with water, dried, filtered and evaporated. The residue was purified by column-chromatography over silica gel using trichloromethane as eluent. The pure fractions were collected and the solvent was evaporated. The residue was crystallized from 1-butanol, yielding 10 g (50.4%) of 4-(4-methoxy-3,5-dimethylphenyl)-1-[(4-methylphenyl)sulfonyl]piperazine; mp. 174.2° C. (interm. 42).

b) A mixture of 77.6 g of intermediate (42), 121.2 ml of concentrated sulfuric acid and 140 ml of water was stirred and refluxed overnight. Another portion of 30.4 g of concentrated sulfuric acid was added and stirring at reflux was continued overnight. The reaction mixture was cooled and treated with sodium hydroxide. The product was extracted with dichloromethane. The extract was washed with water, dried, filtered and evaporated. The residue was converted into the hydrochloric salt in 2-propanol and 2,2'-oxybispropane. The salt was filtered off and crystallized from 2-propanol, yielding 18.5 g of 1-(4-methoxy-3,5-dimethylphenyl)piperazine dihydrochloride (interm. 43).

c) A mixture of 14.1 g of 1-fluoro-4-nitrobenzene, 26 g of intermediate (43), 15 g of sodium carbonate and 272.7 ml of dimethyl sulfoxide was stirred for 4 hours at 60° C. The reaction mixture was cooled and poured into water. The product was extracted with methylbenzene. The extract was washed with water, dried, filtered and evaporated. The residue was triturated in 2,2-oxybispropane. The product was filtered off and crystallized from 2-propanol, yielding 17.5 g (64.1%) of 1-(4-methoxy-3,5-dimethylphenyl)-4-(4-nitrophenyl)piperazine; mp. 135.3° C. (interm. 44).

d) A mixture of 15 g of intermediate (44), 1 ml of a solution of thiophene in methanol (4%) and 202.5 ml of methanol was hydrogenated at normal pressure and at 50° C. with 2 g of palladium-on-charcoal catalyst (10%). After the calculated amount of hydrogen was taken up, the catalyst was filtered off and the filtrate was evaporated. The residue was converted into the hydrochloride salt in 2-propanol. The salt was filtered off and dried, yielding 15.7 g (92.8%) of 4-[4-(4-methoxy-3,5-dimethylphenyl)-1-piperazinyl]-benzenamine dihydrochloride; mp. 289.5° C. (interm. 45).

e) A mixture of 65 g of intermediate (45), 39.3 g of (1-ethoxyethylidene)hydrazine-carboxylic acid ethyl ester and 100 ml of tetrahydrothiophene 1,1-dioxide was stirred for 3 hours at 120° C. under a nitrogen atmosphere. The mixture was cooled and 2-propanol was added. The obtained precipitate was filtered off and dried. The residue was purified by column chromatography (eluent: CHCl$_3$/CH$_3$OH 99:1). The eluent of the desired fraction was evaporated and the residue was crystallized from 1,4-dioxane, yielding 36.75 g (44.9%) of 2,4-dihydro-4-[4-[4-[4-methoxy-3,5-dimethylphenyl)-1-piperazinyl]phenyl]-5-methyl-3H-1,2,4-triazol-3-one; mp. 280.1° C. (interm. 46).

B. Preparation of the Final Compounds

Example 10

A mixture of 2,4-dihydro-4-[6-[4-(4-methoxyphenyl)-1-piperazinyl]-3-pyridinyl]-3H-1,2,4-triazol-3-one (0.014 mol) and sodium carbonate (0.06 mol) in methylbenzene (30 ml) and N,N-dimethylformamide (70 ml) was stirred and refluxed. 2-Bromo-1-(4-chlorophenyl)-1-butanone (0.015 mol) in trichloromethane (20 ml) was added dropwise and the mixture was stirred and refluxed with a water separator for 1 hour. The mixture was filtered warm and the tiltrate was evaporated. The residue was purified by column chromatography over silica gel (eluent: CH$_2$Cl$_2$/CH$_3$OH 98/2). The pure fractions were collected and evaporated. The residue was crystallized from 2-propanol, yielding 6 g (80%) of (±)-2-[1-(4-chlorobenzoyl)propyl]-2,4-dihydro-4-[6-[4-(4-methoxyphenyl)-1-piperazinyl]-3-pyridinyl]-3H-1,2,4-triazol-3-one; mp. 142.4° C. (comp. 1).

In a similar way there were prepared:
(±)-2-[1-(4-chlorobenzoyl)propyl]-2,4-dihydro-4-[5-[4-(4-methoxyphenyl)-1-piperazinyl]-2-pyridinyl]-3H-1,2,4-triazol-3-one; mp. 127.2° C. (comp. 2);
(±)-2-[1-(4-chlorobenzoyl)propyl]-2,4-dihydro-4-[4-[4-(5-methoxy-2-pyridinyl)-1-piperazinyl]phenyl]-3H-1,2,4-triazol-3-one; mp. 165.1° C. (comp. 3);
(±)-2-[1-(4-chlorobenzoyl)propyl]-4-[6-[4-(3-methoxyphenyl)-1-piperazinyl]-3-pyridinyl]-2,4-dihydro-3H-1,2,4-triazol-3-one; mp. 128.3° C. (comp. 4);
(±)-2-[1-(4-chlorobenzoyl)propyl]-2,4-dihydro-4-[6-[4-(2-methoxyphenyl)-1-piperazinyl]-3-pyridinyl]-3H-1,2,4-triazol-3-one; mp. 195.6° C. (comp. 5);
(±)-2-[1-(4-chlorobenzoyl)propyl]-2,4-dihydro-4-[4-[4-(6-methoxy-3-pyridinyl)-1-piperazinyl]phenyl]-3H-1,2,4-triazol-3-one; mp. 188.4° C. (comp. 6);
(±)-2-[1-(4-chlorobenzoyl)propyl]-2,4-dihydro-4-[6-[4-(3-methoxyphenyl)-1-piperidinyl]-3-pyridinyl]-3H-1,2,4-triazol-3-one; mp. 125.7° C. (comp. 7);
(±)-2-[1- (4-chloro benzoyl)propyl]-2,4-dihydro-4-[6-[4-(5-methoxy-2-pyridinyl) -1-piperazinyl]-3-pyridinyl]-3H-1, 2,4-triazol-3-one; mp. 145.9° C. (comp. 37);
(±)-2-[1-(4-chlorobenzoyl)propyl]-2,4-dihydro-4-[4-(4-phenyl-1-piperazinyl)phenyl]-3H-1,2,4-triazol-3-one; mp. 180.7° C. (comp. 39);
(±)-2-[1- (4-chlorobenzoyl)propyl]-4-[6-[4-(2-chlorophenyl)-1-piperazinyl]-3-pyridinyl]2,4-dihydro-3H-1,2,4-triazol-3-one (comp. 41);
(±)-2-[1-(4-chlorobenzoyl)propyl]-2,4-dihydro-4-[6-[4-[3-(trifluoromethyl)phenyl]-1-piperazinyl]-3-pyridinyl]-3H-1,2,4-triazol-3-one; mp. 126.7° C. (comp. 42);
(±)-2-[1-(4-chlorobenzoyl)propyl]-4-[6-[4-(3,5-dimethylphenyl)-1-piperazinyl]-3-pyridinyl]-2,4-dihydro-3H-1,2,4-triazol-3-one dihydrochloride (comp. 43);
(±) -2-[1- (4-chlorobenzoyl)propyl]-4-[6-[4-(3-ethylphenyl)-1-piperazinyl]-3-pyridinyl]-2,4-dihydro-3H-1,2,4-triazol-3-one dihydrochloride (comp. 44);
(±)-2-[1-(4-chlorobenzoyl)propyl]-4-[6-[4-(3,4-dimethoxyphenyl)-1-piperidinyl]-3-pyridinyl]-2,4-dihydxo-3H-1,2,4-triazol-3-one; mp. 107.7° C. (comp. 45); and
(±) -2-[1-(4-chlorobenzoyl)propyl]-4-[6-[4-(3,4-dimethoxyphenyl)-1-piperazinyl]-3-pyridinyl]-2,4-dihydro-3H-1,2,4-triazol-3-one dihydrochloride; mp. 197.3° C. (comp. 48).

Example 11

2,4-Dihydro-4-[2-[4-(4-methoxyphenyl)-1-piperazinyl]-5-pyrimidinyl]-3H-1,2,4-triazol-3-one (0.019 mol) and N,N-dimethylformamide (200 ml) were stirred. A solution of sodium bis(trimethylsilyl)amide in tetrahydrofuran (1M) (21 ml) was added dropwise under N$_2$ and the mixture was stirred for 30 minutes at room temperature. 2-Bromo-1-(4-chlorophenyl)-1-butanone (0.021 mol) dissolved in a little N,N-dimethylformamide was added dropwise and the mixture was stirred for 3 hours at room temperature. The mixture was poured into water and extracted with dichloromethane. The organic layer was washed with water, dried and evaporated. The residue was crystallized from 1-propanol. The precipitate was faltered off and dried in vacuo at 75° C., yielding 6 g (60%) of (±)-2-[1 -(4-chlorobenzoyl)propyl]-2,4-dihydro-4-[2-[4-(4-methoxyphenyl)-1-piperazinyl]-5-pyrimidinyl]-3H-1,2,4-triazol-3-one; mp. 184.6° C. (comp. 8).

Example 12

To a cooled solution (temp -5° C.) of 5.4 g of 1-[1-(4-bromobenzoyl)ethyl]-1,3-dihydro-3-[4-[4-(4-hydroxyphenyl)-1-piperazinyl]phenyl]-2H-imidazol-2-one in 500 ml of tetrahydrofuran were added dropwise 20 ml of a solution of tris(1-methylethoxy)-potassium hydroborate in tetrahydrofuran 1M. After stirring for 2 hours at room temperature, the reaction mixture was diluted with 1500 ml of water and stirring was continued for 2 hours. The precipitate was filtered off, washed with water and dried. The product was recrystallized from 1,4-dioxane. The product was filtered off and dried in vacuo, yielding 3.4 parts (64.5%) of [A]+[B]-1-[2-(4-bromophenyl)-2-hydroxy-1-methylethyl]-1,3-dihydro-3-[4-[4-(4-hydroxyphenyl)-1-piperazinyl]phenyl]-2H-imidazol-2-one; mp. 253.8° C. (comp. 9);

In a similar way there were prepared:

(±)-(R*,R*)-2-[2-(3,4-dichlorophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one hemihydrate; mp. 184.9° C. (comp. 10);

1-[2-(4-chlorophenyl)-2-hydroxy-1-methylethyl]-1,3-dihydro-3-[4-[4-(4-hydroxyphenyl)-1-piperazinyl]phenyl]-4-methyl-2H-imidazol-2-one; mp. 245.7° C. (comp. 11);

1-[2-(4-chlorophenyl)-2-hydroxy-1-methylethyl]-1,3-dihydro-3-[4-[4-(4-hydroxy-phenyl)-1-piperazinyl]phenyl]-2H-imidazol-2-one; mp. 252.8° C. (comp. 12);

(±)-2-[1-[(4-bromophenyl)hydroxymethyl]-1-methylpropyl]-2,4-dihydro-4-[4-[4-(4-hydroxyphenyl)-1-piperazinyl]phenyl]-5-methyl-3H-1,2,4-triazol-3-one; mp. 215.1° C. (comp. 13);

(±)-2-[1-[(4-chlorophenyl)hydroxymethyl]propyl]-2,4-dihydro-4-[6-[4-(4-hydroxyphenyl)-1-piperazinyl]-3-pyridinyl]-3H-1,2,4-triazol-3-one; mp. 231.7° C. (comp. 14);

(±)-(RR,SS)-2-[1-[(4-chlorophenyl)hydroxymethyl]propyl]-2,4-dihydro-4-[4-[4-(5-methoxy-2-pyridinyl)-1-piperazinyl]phenyl]-3H-1,2,4-triazol-3-one; mp. 208.5° C. (comp. 15);

(±)-(R*,R*)-2-[1-[(4-chlorophenyl)hydroxymethyl]propyl]-2,4-dihydro-4-[6-[4-(3-methoxyphenyl)-1-piperazinyl]-3-pyridinyl]-3H-1,2,4-triazol-3-one; mp. 203.8° C. (comp. 16);

(±)-(R*,R*)-2-[1-[(4-chlorophenyl)hydroxymethyl]propyl]-2,4-dihydro-4-[6-[4-(2-methoxyphenyl)-1-piperazinyl]-3-pyridinyl]-3H-1,2,4-triazol-3-one; mp. 199.3° C. (comp. 17);

(±)-(R*,R*)-2-[1-[(4-chlorophenyl)hydroxymethyl]propyl]-2,4-dihydro-4-[6-[4-(3-hydroxyphenyl)-1-piperazinyl]-3-pyridinyl]-3H-1,2,4-triazol-3-one; mp. 240.8° C. (comp. 18);

(±)-(R*,R*)-2-[1-[(4-chlorophenyl)hydroxymethyl]propyl]-2,4-dihydro-4-[6-[4-(2-hydroxyphenyl)-1-piperazinyl]-3-pyridinyl]-3H-1,2,4-triazol-3-one; mp. 221.6° C. (comp. 19);

(±)-(R* ,R*)-2-[1-[(4-chlorophenyl)hydroxymethyl]propyl]-2,4-dihydro-4-[4-[4-(6-methoxy-3-pyridinyl)-1-piperazinyl]phenyl]-3H-1,2,4-triazol-3-one; mp. 209.5° C. (comp. 20);

(±)-(R*,R*)-1-[1-[(4-chlorophenyl)hydroxymethyl]propyl]-1,3-dihydro-3-[6-[4-(4-methoxyphenyl)-1-piperazinyl]-3-pyridinyl]-2H-imidazol-2-one; mp. 192.0° C. (comp. 38); and (±)-(R*,R*)-2-[1-[(4-chlorophenyl)hydroxymethyl]propyl]-2,4-dihydro-4-[4-[4-(6-methoxy-2-pyridinyl)-1-piperazinyl]phenyl]-3H-1,2,4-triazol-3-one; mp. 180.8° C. (comp. 46).

Example 13

A mixture of 2-[2-(4-bromophenyl)-1,1-dimethyl-2-oxoethyl]-2,4-dihydro-4-[4-[4-(4-hydroxyphenyl)-1-piperazinyl]phenyl]-3H-1,2,4-triazol-3-one (0.009 mol) and sodium tetrahydroborate (0.025 mol) in 1,4-dioxane (100 ml), methanol (30 ml) and water (50 ml) was stirred overnight. Acetic acid (5 ml) was added, followed by addition of water (500 ml). Crystallization resulted. The reaction mixture was stirred for 4 hours at room temperature. The precipitate was filtered off by suction (Buchner) and the solid was crystallized from 1-butanol. The precipitate was filtered off and dried, yielding 4.4 g (87%) of (±)-2-[2-(4-bromophenyl)-2-hydroxy-1,1-dimethylethyl]-2,4-dihydro-4-[4-[4-(4-hydroxyphenyl)-1-piperazinyl]phenyl]-3H-1,2,4-triazol-3-one; mp. 224.5° C. (comp. 21).

In a similar way there was prepared:

(±)-2-[2-(4-bromophenyl)-2-hydroxy-1,1-dimethylethyl]-2,4-dihydro-4-[4-[4-(4-hydroxyphenyl)-1-piperazinyl]phenyl]-5-methyl-3H-1,2,4-triazol-3-one; mp. >300° C. (comp. 22);

2,4-dihydro-2-[2-hydroxy-1-methyl-2-(4-methylphenyl)ethyl]-4-[4-[4-(4-hydroxyphenyl)-1-piperazinyl]phenyl]-3H-1,2,4-triazol-3-one; 259.8° C. (comp. 33);

(±)-(R*,R*)-2-[2-(4-bromophenyl)-2-hydroxy-1-methylethyl]-4-[4-[4-[[(1,1-dimethylethyl)dimethylsilyl]oxy]phenyl]-1-piperazinyl]phenyl]-2,4-dihydro-3H-1,2,4-triazol-3-one; mp. 241.3° C. (comp. 34);

(±)-(R* ,R*)-2-[1-[(4-chlorophenyl)hydroxymethyl]butyl]-2,4-dihydro-4-[6-[4-(3-methoxyphenyl)-1-piperazinyl]-3-pyridinyl]-3H-1,2,4-triazol-3-one; mp. 202.4° C. (comp. 40); and (±)-(R*,R*)-2-[1-[(4-chlorophenyl)hydroxymethyl]propyl]-4-[6-[4-(3,4-dimethoxy-phenyl)-1-piperazinyl]-3-pyridinyl]-2,4-dihydro-3H-1,2,4-triazol-3-one (comp. 49).

In a similar way but in the presence of 1-methyl-2-pyrrolidinone instead of 1,4-dioxane was prepared:

2-[2-(4-bromophenyl)-2-hydroxy-1-methylethyl]-2,4-dihydro-4-[6-[4-(4-hydroxy-phenyl)-1-piperazinyl]-3-pyridinyl]-5-methyl-3H-1,2,4-triazol-3-one; mp. 195.1° C. (comp. 23).

Example 14

Sodium sulfite (few crystals) was added to an aqueous hydrobromic acid solution 48% (100 ml) till colourless. (±)-2-[1-(4-chlorobenzoyl)propyl]-2,4-dihydro-4-[5-[4-(4-methoxyphenyl)-1-piperazinyl]-2-pyridinyl]-3H-1,2,4-triazol-3-one (0.0047 mol) was added and the mixture was stirred and refluxed for 2 hours. The mixture was poured into water and neutralized with NH$_4$OH. The precipitate was filtered off and dried. The residue was purified by column chromatography over silica gel (eluent: CH$_2$Cl$_2$/CH$_3$OH 98/2). The pure fractions were collected and evaporated, yielding 2.2 g (90%) of product. A sample (1 g) was crystallized from C$_4$H$_9$OH, yielding 0.7 g of (±)-2-[1-(4-chlorobenzoyl)propyl]-2,4-dihydro-4-[5-[4-(4-hydroxyphenyl)-1-piperazinyl]-2-pyridinyl]-3H-1,2,4-triazol-3-one; mp. 185.6° C. (comp. 24).

In a similar way there were prepared:

(±)-2-[1-(4-chlorobenzoyl)propyl]-2,4-dihydro-4-[6-[4-(4-hydroxyphenyl)-1-piperazinyl]-3-pyridinyl]-3H-1,2,4-triazol-3-one; mp. 185.2° C. (comp. 25);

(±)-2-[1-(4-chlorobenzoyl)propyl]-2,4-dihydro-4-[2-[4-(4-hydroxyphenyl)-1-piperazinyl]-5-pyrimidinyl]-3H-1,2,4-triazol-3-one; mp. 195.3° C. (comp. 26);

(±)-2-[1-(4-chlorobenzoyl)propyl]-2,4-dihydro-4-[4-[4-(5-hydroxy-2-pyridinyl)-1-piperazinyl]phenyl]-3H-1,2,4-triazol-3-one; mp. 193.3° C. (comp. 27);

(±)-2-[1-(4-chlorobenzoyl)propyl]-2,4-dihydro-4-[6-[4-(3-hydroxyphenyl)-1-piperazinyl]-3-pyridinyl]-3H-1,2,4-triazol-3-one; mp. 103.1° C. (comp. 28); and (±)-2-[1-(4-chlorobenzoyl)propyl]-2,4-dihydro-4-[6-[4-(2-hydroxyphenyl)-1-piperazinyl]-3-pyridinyl]-3H-1,2,4-triazol-3-one (comp. 29).

Example 15

To a mixture of 25 g of boron tribromide and 100 ml of dichloromethane was added dropwise a solution of 6.1 g of 1-[1-(4-chlorobenzoyl)ethyl]-1,3-dihydro-3-[4-[4-(4-methoxyphenyl)-1-piperazinyl]phenyl]-4-methyl-2H-imidazol-2-one in 200 ml of dichloromethane (temp<10° C.). After stirring for 2 hours, the reaction mixture was poured into a mixture of NH$_4$OH and ice. Then there were added 300 ml of dichloromethane and the whole was stirred for 1 hour. The organic layer was separated, dried, filtered and evaporated. The residue was purified by column chromatography (silica gel; CH$_2$Cl$_2$/CH$_3$OH 99:1). The eluent of the desired fraction was evaporated and the residue was triturated in methanol. The product was filtered off and dried, yielding 4.3 g (72.3%) of 1-[1-(4-chlorobenzoyl)ethyl]-1,3-dihydro-3-[4-[4-(4-hydroxyphenyl)-1-piperazinyl]phenyl]-4-methyl-2H-imidazol-2-one; mp. 229.7° C. (comp. 30).

In a similar way there was prepared:
2,4-dihydro-4-[4-[4-(4-hydroxyphenyl)-1-piperazinyl]phenyl]-2-[1-(4-methoxy-benzoyl)ethyl]-3H-1,2,4-triazol-3-one; mp. 204.5° C. (comp. 35).

Example 16

A mixture of 2-[1-(4-chlorobenzoyl)propyl]-2,4-dihydro-4-[4-[4-(4-hydroxyphenyl)-1-piperazinyl]phenyl]-3H-1,2,4-1-triazol-3-one (0.009 mol) and benzyltriethylammonium chloride (0.25 g) in dichloromethane (150 ml) was stirred. Sodium hydroxide 25% (50 ml) was added and the mixture was stirred for 10 minutes. Dimethyl sulfate (0.015 mol) was added and the mixture was stirred at room temperature for 1 hour. The mixture was diluted with water (100 ml) and separated. The organic layer was washed with water and dried. The residue was purified by column chromatography over silica gel (eluent: CH$_2$Cl$_2$/CH$_3$OH 98/2). The pure fractions were collected and evaporated, yielding 4.3 g of product. This fraction was purified by column chromatography CHIRACEL OD® (1 kg) (eluent: C$_2$H$_5$OH). The pure fractions were collected and evaporated, yielding 0.9 g (+)-(A)-2-[1-(4-chlorobenzoyl)propyl]-2,4-dihydro-4-[4-[4-(4-methoxyphenyl)-1-piperazinyl]phenyl]-3H-1,2,4-triazol-3-one; mp. 199.6° C.; $[\alpha]_D$=163.01° (comp. 31).

Example 17

(±)-(R*,R*)-2-[2-(2,4-dichlorophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one monohydrate (1.5 g) was purified by column chromatography CHIRACEL OD® (1 kg) (eluent: n.hexane/2-propanol 80:20). The pure fractions were collected and evaporated. The residue was crystallized from 2-propanol, yielding 0.5 g of (+)-(R*,R*)-2-[2-(2,4-dichlorophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one dihydrate; mp. 123.5° C.; $[\alpha]_D^{20}$=+28.2° (comp. 32).

Example 18

A mixture of (±)-4-[4-[4-[4-[[( 1,1-dimethylethyl)dimethylsilyl]oxy]phenyl]-1-piperazinyl]phenyl]-2,4-dihydro-2-[2-hydroxy-2-[4-(trifluoromethoxy)phenyl]ethyl]-5-methyl-3H-1,2,4-triazol-3-one (0.0043 mol) was dissolved in dichloromethane (100 ml) upon stirring. A solution of tetrabutylammonium fluoride in tetrahydrofuran (0.0045 mol) was added and the mixture was stirred at room temperature for 15 minutes. Water was added and the mixture was stirred for 30 minutes. The precipitate was filtered off, dried and crystallized from n-butanol, yielding 1.1 g (58.2%) of (±)-2,4-dihydro-4-[4-[4-(4-hydroxyphenyl)-1-piperazinyl]phenyl]-2-[2-hydroxy-2-[4-(trifluoromethoxy)-phenyl]ethyl]-5-methyl-3H-1,2,4-triazol-3-one; mp. 230.6° C. (comp. 36).

Example 19

A solution of 2-(chlorodimethylsilyl)-2-methylpropane (0.011 mol) in dichloromethane (20 ml) was added to a stirred solution of 2-[1-(4-bromobenzoyl)ethyl]-2,4-dihydro-4-[4-[4-(4-hydroxyphenyl)-1-piperazinyl]phenyl]-3H-1,2,4-triazol-3-one (0.009 mol) in pyridine (20 ml) under a nitrogen atmosphere. Stirring was continued for 1 week at room temperature. The reaction mixture was evaporated and the residue was dissolved in dichloromethane. This solution was purified over silica gel on a glass filter (eluent: dichloromethane). The pure fractions were collected and the solvent was evaporated. The residue (3.5 g) was recrystallized from ethyl acetate. The product was filtered off and dried, yielding 2.7 g (45 %) of 2-[1-(4-bromobenzoyl)ethyl]-4-[4-[4-[[( 1,1-dimethylethyl)dimethylsilyl]oxy]phenyl]-1-piperazinyl]phenyl]-2,4-dihydro-3H-1,2,4-triazol-3-one; mp. 177.8° C. (comp. 47).

C. Pharmacological Example

The anti-Helicobacter activity of the subject compounds was assessed by the following in-vitro test procedure.

Activity of Test Compounds Versus Helicobacter

The activity of test compounds against Helicobacter pylori was determined against a standard set of 5 H. priori strains obtained from clinical material. Minimal inhibitory concentrations (MICs) were determined by measuring the activity of H. pylori urease after treatment of growing cultures of the bacteria with the antimicrobial agents.

The test compounds were dissolved in DMSO at a concentration of $10^{-3}$M. A dilution to $10^{-4}$M in DMSO was also prepared. 10 μl volumes of these solutions were pipetted in the wells of Repli-Dishes (®Sterilin). Wells containing DMSO alone were included as controls in each Repli-Dish. Ampicillin ((+)-6-[(2-amino-2-phenylacetyl)amino]-3,3-dimethyl-7-oxo-4-thia-1-azabicyclo[3.2.0]heptane-2-carboxylic acid trihydrate) and metronidazole (2-methyl-5-nitro-1H-imidazol-1-ethanol) were included as reference compounds in each batch of tests. (These compounds were tested at final concentrations of $10^{-5}$, $10^{-6}$, $10^{-7}$ and $10^{-8}$M). Test plates were stored at 4° C. until used. The five isolates of H. pylori were maintained by subculture on 10% blood agar every 2 or 3 days. The bacteria were grown at 37° C. under an atmosphere containing 5% oxygen, 10% CO$_2$ and 85% nitrogen. Suspensions of Helicobacter pylori for inoculum were prepared in Brain-heart infusion broth and adjusted to an absorbance of 1.5±0.3 at 530 nM.

Freshly prepared 10% blood agar held at 45° C. was added in 1 ml volumes to the wells of the test plates, thus diluting the test compounds to $10^{-5}$ and $10^{-6}$M. The medium was allowed to cool, then 10 μl volumes of bacterial suspension were pipetted on the agar surface. The plates were incubated for 48 h at 37° C. under the microaerophilic atmosphere described above. To facilitate reading of the plates and to ensure that any growth on the media was truly H. pylori, advantage was taken of the highly potent urease activity unique to this species. After the 48 h of incubation, 1 ml volumes of urease broth were gently added to each Repli-Dish well and the plates were incubated at 37° C. for 2 h. 100 µl samples of fluid from each well were then pipetted into the wells of 96-place microdilution plates. A purple colour was interpreted as growth, yellow-orange as no growth of H. pylori. By this means a clear end-point was obtained, from which the inhibitory effects could be determined. All compounds that showed activity at either of the two concentrations tested was retested with further dilutions included to establish the MIC and with a broader spectrum of bacterial species as target organisms.

Table 1 summarizes the MIC values determined by the above procedure for a subset of the subject compounds.

TABLE 1

| Comp. No. | MIC (µM) | Comp. No. | MIC (µM) |
|---|---|---|---|
| 1 | 0.1 | 25 | 0.1 |
| 2 | 10 | 26 | 0.1 |
| 3 | 0.1 | 27 | 0.1 |
| 4 | 0.01 | 28 | 0.01 |
| 5 | 0.1 | 29 | 0.1 |
| 6 | 0.1 | 30 | 1 |
| 7 | 0.1 | 31 | 1 |
| 8 | 0.1 | 32 | 1 |
| 9 | 1 | 33 | 1 |
| 10 | 1 | 34 | 1/0.1 |
| 11 | 1 | 35 | 10 |
| 12 | 0.1 | 36 | 10 |
| 13 | 0.1 | 37 | 0.1 |
| 14 | 0.1 | 38 | 0.1 |
| 15 | 0.1 | 39 | 1/0.01 |
| 16 | 0.1/0.01 | 40 | 0.1 |
| 17 | 0.1 | 41 | 1/0.1 |
| 18 | 0.1/0.01 | 42 | 1/0.01 |
| 19 | 0.1/1 | 43 | 1/0.1 |
| 20 | 0.1/0.01 | 44 | 1/0.1 |
| 21 | 0.1 | 45 | 0.01 |
| 22 | 1 | 46 | 1/0.1 |
| 23 | 1 | 47 | 1 |
| 24 | 1/0.1 | 48 | ≦0.001 |
|  |  | 49 | 0.01 |

D. Composition Examples

"Active ingredient" (A.I.) as used throughout these examples relates to a compound of formula (I), a pharmaceutically acceptable acid addition salt or a stereochemically isomeric form thereof.

Example 20: Oral Drops

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 21: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

Example 22: Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 23: Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 l, giving a solution comprising 4 mg/ml of A.I.. The solution was sterilized by filtration and filled in sterile containers.

Example 24: Suppositories

3 Grams A.I. was dissolved in a solution of 3 grams 2,3-dihydroxybutanedioic acid in 25 ml polyethylene glycol 400. 12 Grams surfactant and triglycerides q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

Example 25: Cyclodextrin Containing Formulation 100 ml of propylene glycol is treated with 3.76 ml concentrated HCl, stirred and slightly heated. 10 g A.I. is added and stirring is continued until homogeneous. In a separate vessel, 400 g hydroxypropyl-13-cyclodextrin is dissolved in 400 ml distilled water. The solution of the active ingredient is added slowly to the cyclodextrin solution while stirring. The sorbitol solution (190 ml) is added and stirred till homogeneous. The sodium saccharin (0.6 g) is dissolved in 50 ml distilled water and added to the mixture. The flavours are added and the pH of the mixture (about 1.7) is adjusted with a 10N NaOH solution to pH 2.0±0.1. The resulting solution is diluted with distilled water to an end volume of 1 liter. A pharmaceutical dosage form is obtained by filtering the previous solution and filling it into suitable containers, e.g. in 100 ml glass bottles with a screw cap.

We claim:

1. A method of treating subjects suffering from Helicobacter-related diseases which comprises administering to said subjects an effective anti-Helicobacter amount of a compound of the formula:

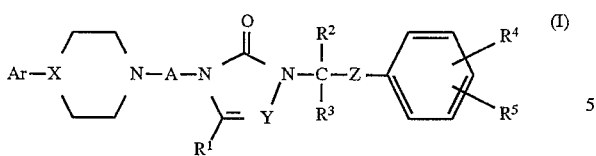

a pharmaceutically acceptable acid addition salt or a stereochemically isomeric form thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

Z is C=O or CHOH; and

Ar is phenyl optionally substituted with up to three substituents selected from hydroxy, $C_{1-4}$alkyl, $C_{1-4}$alkyloxy, halo, trifluoromethyl, tri$C_{1-4}$alkylsilyloxy, nitro, amino and cyano or pyridinyl substituted with hydroxy or $C_{1-4}$alkyloxy; and —A— is a group of formula

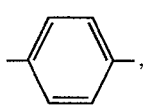 (a-1)

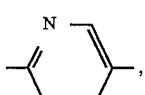 (a-2)

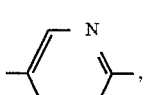 (a-3)

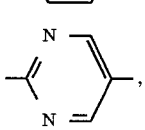 (a-4)

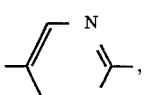 (a-5)

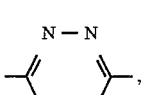 (a-6)

or

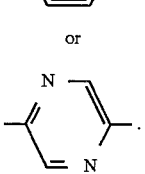 (a-7)

2. A method according to claim 1 of a compound of formula (I) wherein Ar is a group of formula

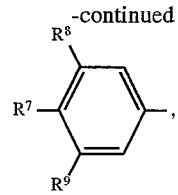 (b-1)

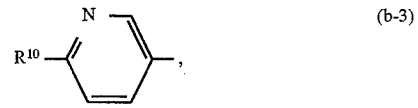 (b-2)

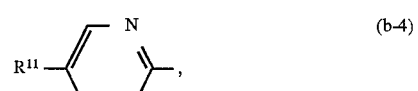 (b-3)

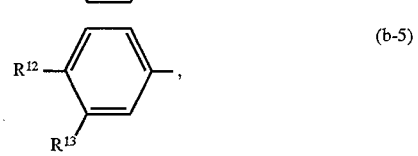 (b-4)

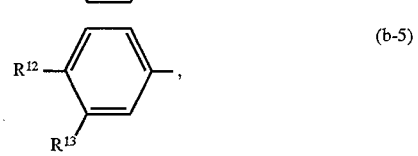 (b-5)

wherein $R^6$, $R^7$, $R^{10}$, $R^{11}$, $R^{12}$ and $R^{13}$ each independently are hydroxy or $C_{1-4}$alkyloxy; and $R^8$ and $R^9$ are $C_{1-4}$alkyl.

3. A method according to claim 1 of a compound of formula (I) wherein —A— is a group of formula (a-1), (a-2) or (a-3).

4. A method according to claim 1 of a compound of formula (I) wherein $R^2$ is $C_{1-4}$alkyl; $R^4$ is halo substituted at the para position; and $R^1$, $R^3$ and $R^5$ are hydrogen.

5. A method according to claim 4 of a compound of formula (I) wherein Ar is hydroxyphenyl, methoxyphenyl, dimethoxyphenyl, $C_{1-4}$alkylphenyl, di$C_{1-4}$alkylphenyl or methoxypyridinyl.

6. A compound of the formula:

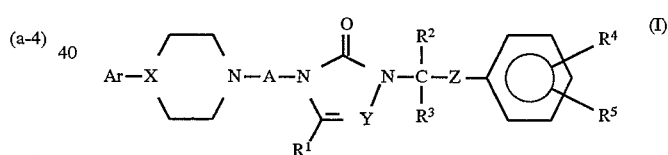 (I)

a pharmaceutically acceptable acid addition salt thereof or a stereochemically isomeric form thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

Z is C=O or CHOH;

Ar is (a) phenyl optionally substituted with up to three substituents selected from hydroxy, $C_{1-4}$alkyl, $C_{1-4}$alkyloxy, trifluoromethyl, tri$C_{1-4}$alkylsilyloxy, nitro, amino and cyano, or (b) pyridinyl substituted with hydroxy or $C_{1-4}$alkyloxy; and —A— represents a group of the formula:

 (a-1)

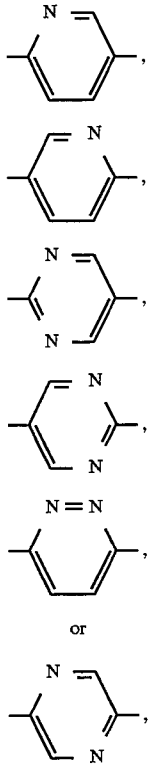

(a-2)

(a-3)

(a-4)

(a-5)

(a-6)

or (a-7)

provided that Ar is other than 4-hydroxyphenyl, 3-C$_{1-4}$alkyl-4-hydroxy-phenyl or 3,5-di(C$_{1-4}$alkyl)-4-hydroxyphenyl when X=N and

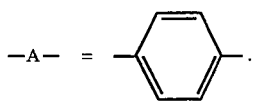

(a-1)

7. A pharmaceutical composition comprising a pharmaceutically acceptable carrier and as active ingredient a therapeutically effective amount of a compound as defined in claim 6.

8. A compound of the formula:

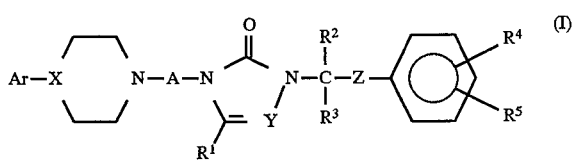

(I)

a pharmaceutically acceptable acid addition salt thereof or a stereochemically isomeric form thereof, wherein X and Y each independently are CH or N;

R$^1$, R$^2$ and R$^3$ each independently are hydrogen or C$_{1-4}$alkyl;

R$^4$ and R$^5$ each independently are hydrogen, halo, C$_{1-4}$alkyl, C$_{1-4}$alkyloxy, hydroxy, trifluoromethyl, trifluoromethyloxy or difluoromethyloxy;

Z is C=O or CHOH;

Ar is (a) phenyl optionally substituted with up to three substituents selected from hydroxy, C$_{1-4}$alkyl, C$_{1-4}$alkyloxy, halo, trifluoromethyl, triC$_{1-4}$alkylsilyloxy, nitro, amino and cyano, or (b) pyridinyl substituted with hydroxy or C$_{1-4}$alkyloxy; and —A— is a group of the formula:

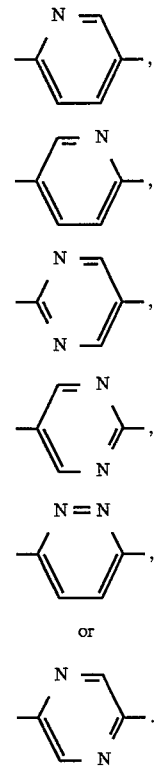

(a-2)

(a-3)

(a-4)

(a-5)

(a-6)

or (a-7)

9. A pharmaceutical composition comprising a pharmaceutically acceptable carrier and as active ingredient a therapeutically effective amount of a compound as defined in claim 8.

10. A compound of the formula:

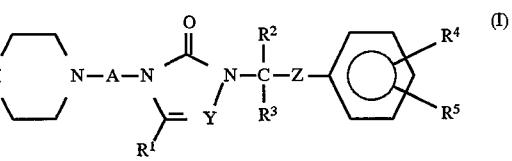

(I)

a pharmaceutically acceptable acid addition salt thereof or a stereochemically isomeric form thereof, wherein X and Y each independently are CH or N;

R$^1$, R$^2$ and R$^3$ each independently are hydrogen or C$_{1-4}$alkyl;

R$^4$ and R$^5$ each independently are hydrogen, halo, C$_{1-4}$alkyl, C$_{1-4}$alkyloxy, hydroxy, trifluoromethyl, trifluoromethyloxy or difluoromethyloxy;

Z is C=O or CHOH;

Ar is (a) phenyl optionally substituted with up to three substituents selected from hydroxy, C$_{1-4}$alkyl, C$_{1-4}$alkyloxy, trifluoromethyl, triC$_{1-4}$alkylsilyloxy, nitro, amino and cyano, or (b) pyridinyl substituted with hydroxy or C$_{1-4}$alkyloxy; and

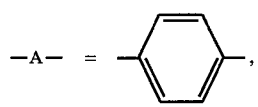

(a-1)

provided that Ar is other than 4-hydroxyphenyl, 3-C$_{1-4}$alkyl-4-hydroxy-phenyl or 3,5-di(C$_{1-4}$alkyl)-4-hydroxyphenyl when X=N.

11. A pharmaceutical composition comprising a pharmaceutically acceptable carrier and as active ingredient a therapeutically effective amount of a compound as defined in claim 10.

12. A compound of the formula:

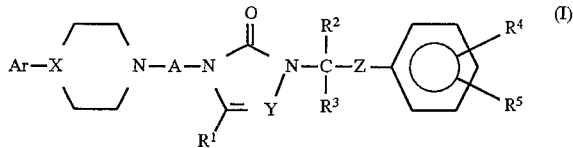

a pharmaceutically acceptable acid addition salt thereof or a stereochemically isomeric form thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

Z is C=O or CHOH;

Ar is (a) phenyl optionally substituted with up to three substituents selected from hydroxy, $C_{1-4}$alkyl, halo, $C_{1-4}$alkyloxy, trifluoromethyl, tri$C_{1-4}$alkylsilyloxy, nitro, amino and cyano, or (b) pyridinyl substituted with hydroxy or $C_{1-4}$alkyloxy; and

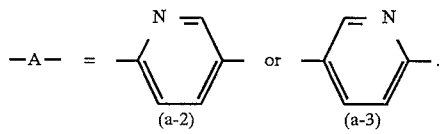

13. A pharmaceutical composition comprising a pharmaceutically acceptable carrier and as active ingredient a therapeutically effective amount of a compound as defined in claim 12.

14. A compound according to claim 6 wherein said compound is

2-[1-(4-chlorobenzoyl)propyl]-2,4-dihydro-4-[6-[4-(4-methoxyphenyl)-1-piperazinyl]-3-pyridinyl]-3H-1,2,4-triazol-3-one;

2-[1-(4-chlorobenzoyl)propyl]-2,4-dihydro-4-[6-[4-(3-hydroxyphenyl)-1-piperazinyl]-3-pyridinyl]-3H-1,2,4-triazol-3-one;

2-[1-[(4-chlorophenyl)hydroxymethyl]propyl]-2,4-dihydro-4-[6-[4-(3-hydroxyphenyl)-1-piperazinyl]-3-pyridinyl]-3H-1,2,4-triazol-3-one;

2-[1-[(4-chlorophenyl)hydroxymethyl]propyl]-2,4-dihydro-4-[4-[4-(6-methoxy-3-pyridinyl)-1-piperazinyl]phenyl]-3H-1,2,4-triazol-3-one;

2-[1-(4-chlorobenzoyl)propyl]-4-[6-[4-(3-methoxyphenyl)-1-piperazinyl]-3-pyridinyl]-2,4-dihydro-3H-1,2,4-triazol-3-one;

2-[1-[(4-chlorophenyl)hydroxymethyl]propyl]-2,4-dihydro-4-[6-[4-(3-methoxyphenyl)-1-piperazinyl]-3-pyridinyl]-3H-1,2,4-triazol-3-one;

2-[1-(4-chlorobenzoyl)propyl]-4-[6-[4-(3,4-dimethoxyphenyl)-1-piperidinyl]3-pyridinyl]-2,4-dihydro-3H-1,2,4-triazol-3-one;

2-[1-[(4-chlorophenyl)hydroxymethyl]propyl]-2,4-dihydro-4-[4-[4-(6-methoxy-2-pyridinyl)-1-piperazinyl]phenyl]-3H-1,2,4-triazol-3-one;

2-[1-[(4-chlorophenyl)hydroxymethyl]propyl]-4-[6-[4-(3,4-dimethoxyphenyl)-1-piperazinyl]-3-pyridinyl]-2,4-dihydro-3H-1,2,4-triazol-3-one;

2-[1-(4-chlorobenzoyl)propyl]-4-[6-[4-(3,4-dimethoxyphenyl)-1-piperazinyl]-3-pyridinyl]-2,4-dihydro-3H-1,2,4-triazol-3-one, a pharmaceutically acceptable acid addition salt or a stereochemically isomeric form thereof.

* * * * *